US010569262B2

(12) United States Patent
Launay et al.

(10) Patent No.: US 10,569,262 B2
(45) Date of Patent: Feb. 25, 2020

(54) BUTADIENE TELOMERIZATION CATALYST PRECURSOR PREPARATION

(71) Applicant: Dow Global Technologies LLC, Midland, MI (US)

(72) Inventors: Helene N. Launay, Ghent (BE); Jessica L. Klinkenberg, Midland, MI (US); John R. Briggs, Midland, MI (US); Sarah E. House, Lake Jackson, TX (US); Marcel C. Van Engelen, Goes (NL); Larry G. Wright, Midland, MI (US); Georg Bar, Markkleeberg (DE); Wilma Hansen, Terneuzen (NL); Julia Cabello Fuertes, Ghent (BE); Istvan Lengyel, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/030,625

(22) PCT Filed: Dec. 4, 2014

(86) PCT No.: PCT/US2014/068483

§ 371 (c)(1),
(2) Date: Apr. 20, 2016

(87) PCT Pub. No.: WO2015/088867

PCT Pub. Date: Jun. 18, 2015

(65) Prior Publication Data

US 2016/0271601 A1 Sep. 22, 2016

Related U.S. Application Data

(60) Provisional application No. 61/915,781, filed on Dec. 13, 2013.

(51) Int. Cl.
*C07C 11/02* (2006.01)
*B01J 31/24* (2006.01)
*C07F 15/00* (2006.01)

(52) U.S. Cl.
CPC ....... *B01J 31/2438* (2013.01); *B01J 31/2404* (2013.01); *C07F 15/006* (2013.01); *B01J 2231/20* (2013.01); *B01J 2531/824* (2013.01)

(58) Field of Classification Search
None
See application file for complete search history.

(56) References Cited

U.S. PATENT DOCUMENTS

| | | | |
|---|---|---|---|
| 8,558,030 B2 | 10/2013 | Briggs et al. |
| 2016/0271601 A1 | 9/2016 | Launay et al. |

FOREIGN PATENT DOCUMENTS

| | | | |
|---|---|---|---|
| EP | 0450707 A1 | 10/1991 |
| EP | 561779 A1 | 9/1993 |
| WO | 2012087686 A1 | 6/2012 |
| WO | 2016164258 A1 | 10/2016 |

OTHER PUBLICATIONS

Arno Behr, et al., Octadienyl-Bridged Bimetallic Complexes of Palladium as Intermediates in Telomerization Reactions of Butadiene, 1986, pp. 514-518, vol. 5.

Frank Vollmüller, et al., Advanced Synthesis & Catalysis, 2001, pp. 29-33, vol. 343.

Frank Vollmüller, et al., European Journal of Inorganic Chemistry, 2000, pp. 1825-1832.

Peter J.C. Hausoul, et al., Facile Access to Key Reactive Intermediates in the Pd/PR3-Catalyzed Telomerization of 1,3-Butadiene, 2010, pp. 7972-7975, vol. 49.

Peter J.C. Hausoul, et al., Mechanistic Study of the Pd/TOMPP-Catalyzed Telomerization of 1,3-Butadiene with Biomass-Based; Alcohols: On the Reversibility of Phosphine Alkylation, 2011, pp. 845-852, vol. 3.

Peter J.C. Hausoul, et al., Organometallics, 2013, pp. 5047-5057, vol. 32.

R. Benn, et al., Organometallics, 1985, pp. 1945-1953, vol. 4.

Ralf Jackstell, et al., An Industrially Viable Catalyst System for Palladium-Catalyzed Telomerizations of 1,3-Butadiene with Alcohols, 2004, pp. 3891-3900, vol. 10.

International Search Report and Written Opinion for PCT/US2014/068483, dated Sep. 2015, pp. 1-14.

International Preliminary Report on Patentability for PCT/US2014/068483, dated Jun. 2016, pp. 1-10.

U. Storzer, et al., Organometallics, 2005, pp. 514-520, vol. 24.

Chinese First Office Action dated Mar. 30, 2018 pertaining to Chinese Patent App. No. 201480066623.7, 6 Pages.

Brenstrum et al., "Phosphaadamantanes as Ligands for Palladium Catalyzed Cross-Coupling Chemistry: Library Synthesis, Characterization, and Screening in the Suzuki Coupling of Alkyl Halides and Tosylates Containing 6-Hydrogens with Boronic Acids and Alkylboranes", J. Org. Chem., 2004, 69, 7635-7639.

Epstein et al., "A Novel Phosphorous Heterocyclic System for the Reactions of Phosphine and Primary Phosphines with 2,4-Pentanedione", J. Am. Chem. Soc., 1967, 83, 3279-3282.

International Preliminary Report on Patentability pertaining to PCT/US2016/025472 dated Oct. 10, 2017.

International Search Report and Written Opinion pertaining to PCT/US2016/025472 dated Jul. 11, 2016.

Protopopov et al., "Reactions of Phenol Ethers with Phosphorous Trichloride 11: Reaction of m-Dimethozybenzene with Phosphorus Trichloride", Zhumal Obshchei Khimii, 1964, 34, 1446-1449.

Office Action pertaining to U.S. Appl. No. 15/564,543 dated Oct. 9, 2018.

Office Action dated Apr. 18, 2019 pertaining to U.S. Appl. No. 15/564,543, filed Oct. 5, 2017, 11 pgs.

Examination Report pertaining to European Patent Application No. 14827296.6, dated May 15, 2019.

Office Action pertaining to corresponding Chinese Patent Application No. 201680020659.0, dated Jun. 17, 2019, received Jul. 22, 2019.

*Primary Examiner* — Yun Qian
(74) *Attorney, Agent, or Firm* — Dinsmore & Shohl LLP

(57) ABSTRACT

Use a solvent blend that contains 1-methoxy-2,7-octadiene and an alkanols rather than the alkanols by itself to prepare a catalyst precursor suitable for use in butadiene telomerization.

9 Claims, No Drawings

BUTADIENE TELOMERIZATION CATALYST PRECURSOR PREPARATION

The present application claims the benefit of U.S. Provisional Application No. 61/915,781, filed on Dec. 13, 2013.

This invention relates generally to preparation of a butadiene telomerization catalyst precursor.

U.S. Pat. No. 8,558,030 B2 discloses a process for telomerizing butadiene that includes contacting butadiene and an organic hydroxyl compound represented by formula ROH, where R is a substituted or unsubstituted $C_1$-$C_{20}$ hydrocarbyl and the organic hydroxyl compound is not glycerol in a reaction fluid in the presence of a palladium catalyst and a phosphine ligand represented by formula $PAr_3$, wherein each Ar is independently a substituted or unsubstituted aryl having a hydrogen atom on at least one ortho position, at least two Ar groups are ortho-hydrocarbyloxyl substituted aryls. The phosphine ligand has a total of 2, 3, 4, 5 or 6 substituted or unsubstituted $C_1$-$C_{20}$ hydrocarbyloxyls and, optionally, two adjacent substituents on an Ar group can be bonded to form a 5- to 7-membered ring.

A typical process for preparing a catalyst precursor used in telomerization of butadiene to produce 1-octene involves batchwise dissolution of one equivalent of palladium acetyl acetonate ($[Pd(acac)_2]$) and two equivalents of a triarylphosphine ($PAr_3$) (e.g. triphenyl phosphine (TPP) or tris(5-chloro-2-methoxyphenyl)phosphine (TCMPP)) in methanol. This precursor is stabilized by acetic acid that is also added during pre-catalyst solution make-up, resulting in a salt that is soluble in methanol and in a +2 oxidation state. Under telomerization reaction conditions, the palladium (Pd) (II)-containing catalyst precursor appears to be reduced by a sodium methoxide promoter in methanol in the presence of 1,3-butadiene to a palladium(0) bis phosphine complex designated as $[Pd(PPh_3)_2]$. Subsequent addition of 1,3-butadiene results in formation of a $(PPh_3)_{1\ or\ 2}$-Pd-(octadienyl) complex. Further reaction with methanol leads to formation of either 1-methoxy-2,7-octadiene (MOD-1) or 3-methoxy-1,7-octadiene (MOD-3). At low temperatures such as those within a range of from 25° centigrade (° C.) to 60° C., the reaction can include an induction period due to reduction of the Pd(II) species to an active Pd(0) complex. This reduction can occur more slowly than the telomerization reaction, and therefore results in an induction period before the telomerization reaction attains maximum rate. A desire exists to reduce, preferably substantially reduce and more preferably eliminate the induction period.

Hausoul et al. in "Facile Access to Key Reactive Intermediates in the Pd/$PR_3$—Calalyzed Telomerization of 1,3-Butadiene", *Angew. Chem. Int. Ed,* 2010, 49, 7971-7975, notes that Pd-catalyzed telomerization of 1,3-dienes is an important atom-efficient transformation that provides an economically attractive route to production of $C_8$ bulk chemicals such as 1-octanol and 1-octene. Hausoul reports on preparation of catalyst complexes that include phosphine ligands such as $PPh_3$ (triphenylphosphine), TOMPP (tris(2-methoxyphenyl)phosphine) and TPPTS (3,3',3''-phosphinidynetris(benzenesulfonic acid) trisodium salt). The preparation uses a solvent mixture such as a 1:1 volume mixture of dichloromethane and methanol.

Benn et al., in "Intermediates in the Palladium-Catalyzed Reactions of 1,3-Dienes. 2. Preparation and Structure of ($\eta^1$,$\eta^3$-Octadiendiyl)palladium Complexes", *Organometallics* 1985, 4, 1945-1953, reports preparation of a series of ($\eta^1$,$\eta^3$-octadiendiyl)palladium complexes, $[Pd(L)(\eta^1,\eta^3\text{-}C_8H_{12})]$ and $[Pd(L)(\eta^1,\eta^3\text{-}Me_2C_8H_{10})]$ by reacting bis($\eta^3$-2-methylallyl) palladium with donor ligands and butadiene or isoprene and tetrahydrofuran (THF) as a solvent.

Behr et al., in "Octadienyl-Bridged Bimetallic Complexes of Palladium as Intermediates in Telomerization Reactions of Butadiene", *Organometallics* 1986, 5, 514-518, discusses preparation of title compounds using a solvent such as methanol, THF or benzene.

Hausoul et al., in "Mechanistic Study of the Pd/TOMPP-Catalyzed Telomerization of 1,3-Butadiene with Biomass-Based Alcohols: On the Reversibility of Phosphine Alkylation", *Chem Cat Chem* 2011, 3, 845-852, discloses testing of several catalyst systems with emphasis upon Pd/TOMPP (tris(2-methoxyphenyl)phosphine).

Vollmüller et al, in Palladium-Catalyzed Reactions for the Synthesis of Fine Chemicals, 16, Highly Efficient Palladium-Catalyzed Telomerization of Butadiene with Methanol", Adv. Synth. Catal. 2001, 343, No. 1, pages 29-33, details use of methanol under argon to prepare a catalyst precursor from triphenylphosphine and palladium(II) acetate.

Jackstell et al., in "An Industrially Viable Catalyst System for Palladium-Catalyzed Telomerizations of 1,3-Butadiene with Alcohols", *Chem. Eur. J.* 2004, 10, 3891-3900, describe use of methanol in preparation of catalyst precursors.

Vollmüller et al., in "Palladium-Catalyzed Reactions for the Synthesis of Fine Chemicals, 14, Control of Chemo- and Regioselectivity in the Palladium-Catalyzed Telomerization of Butadiene with Methanol—*Catalysis and Mechanism,* 2000, 8, 1825-1832, uses mono(phosphane)palladium(0)-diallyl ether complexes, $Ar_3P—Pd(CH_2{=}CHCH_2)_2O$, as catalysts to dimerize 1,3-diene, specifically butadiene, in the presence of a nucleophile, in this case methanol. MOD-1 is a primary product, but MOD-3 and other materials are present as byproducts. Vollmüller et al. states that the catalyst does not need to be activated (e.g. by ligand dissociation, reduction, etc.) before entering the catalyst cycle, but does not discuss precatalyst stability.

Hausoul et al., in "Mechanistic study of the Pd/TOMPP-Catalyzed Telomerization of 1,3-Butadiene: Influence of Aromatic Solvents on Bis-Phosphine Complex Formation and Regio Selectivity", *Organometallics,* 2013, 32, pages 5047-5057, reports on Pd/TOMPP-catalyzed telomerization of 1,3-butadiene with phenols such as p-cresol, guaiacol and creosol.

European Patent Specification (EP) 0 561 779 B1 (Bohley et al.) relates to a process for producing 1-octene. The process comprises: i) reacting 1,3-butadiene with a primary aliphatic alcohol (e.g. methanol, ethanol, propanol, butanol, ethylene glycol, propylene glycol and glycerol) or aromatic hydroxyl compound having formula R—H (e.g. phenol, benzylalcohol, cresols, xylenols, naphthol, polyhydric compounds such as resorcinol, hydroquinone and pyrocatechol as well as alkyl-, alkoxy- and/or halogen-substituted aromatic compounds such as methoxyphenol and p-chlorophenol) in the presence of a telomerization catalyst comprising palladium and a tertiary phosphorous ligand compound to form a 1-substituted-2,7-octadiene of formula $CH_2{=}CH—CH_2—CH_2—CH_2—CH{=}CH—CH_2—R$ in which R represents the residue of the primary aliphatic alcohol or aromatic hydroxy compound; ii) subjecting the 1-substituted-2,7-octadiene to hydrogenation in the presence of a hydrogenation catalyst to form a 1-substituted octane of formula $CH_3—CH_2—CH_2—CH_2—CH_2—CH_2—CH_2—CH_2—R$; and iii) decomposing the 1-substituted octane in the presence of a suitable catalyst to form 1-octene. Both palladium (II) compounds and palladium(0) complexes may be used as the catalyst. A catalyst promoter such as an alkali or alkaline earth metal salt appears to be advantageous. '779 teaches that any solvent that will solubilize 1,3-butadiene, the active hydrogen-containing compound and the catalyst, ligand and optional promoter components may be used in the process. Suitable inert solvents are (cyclo)-alkanes, aromatic compounds, a polar solvent such as a tertiary alcohol, an amide, a nitrile compound, a ketone, an ester compound, an ether compound, dimethylsulfoxide, sulpholane, and water. While the temperature is not critical, it is normally between ambient temperature and 150° C., preferably 50-100° C., and more preferably 70-100° C. Pressure is not critical, but is generally between 1 and 40 bars, preferably between 5 and 30 bars and most preferably between 10 and 20 bars.

In some aspects, this invention is a process for preparing a telomerization catalyst precursor used in telomerization of butadiene that comprises dissolving one equivalent of palladium acetyl acetonate and from one to three equivalents of a phosphine in a solvent blend that comprises methanol and 1-methoxy-2,7-octadiene under conditions sufficient to yield a catalyst precursor solution that comprises an aryl phosphine-palladium octadienyl complex represented formulaically either as $[(Ar_nPR_{(3-n)})_xPdY]$ or as $[(Ar_nPR_{(3-n)})_xPdY]^+$ wherein R is an alkyl or heteroatom-containing alkyl moiety with 1 to 12 carbon atoms, Ar is an aryl moiety or substituted aryl moiety, x=1 or 2, n=1, 2 or 3, and Y is a ligand derived from methoxyoctadiene and wherein illustrative ligands include 1-methoxy-2,7-octadiene (MOD-1) where no charge is present or octadienyl when a positive charge is present. The catalyst precursor resulting from this process surprisingly enters directly into a telomerization reactor's catalytic cycle with no activation step or induction period required. Elimination of the activation step equates to increases in conversion and capacity. In addition, this catalyst precursor is more stable than a catalyst precursor prepared in the absence of 1-methoxy-2,7-octadiene (MOD-1). Under normal pre-catalyst storage conditions (Pd content of 0.1 wt % to 1 wt %, temperature within a range of from 0° C. to 100° C., preferably from 5° C. to 60° C. and pressure within a range of from 0 psig (0 KPa) to 30 psig (206.8 KPa)), Pd(II) complexes are reduced slowly to neutral Pd (0) complexes such as $Pd(PPh_3)_3$ or $Pd(TCMPP)_2(CH_2{=}C\{(C{=}O)Me\}_2$. These Pd complexes are substantially less soluble in methanol than the initially formed Pd complex and can precipitate on process equipment surfaces with which they come in contact, leading to plugging. The addition of MOD-1 imparts a degree of resistance to formation of such insoluble complexes, thereby improving process operability and reliability relative to catalyst precursor preparation with only methanol as a solvent.

In some aspects, this invention is a process for preparing a telomerization catalyst precursor used in telomerization of butadiene that comprises dissolving one equivalent of palladium acetyl acetonate and from one to three equivalents, preferably from one to two equivalents, of a tertiary phosphine ligand in a solvent that comprises methanol and, optionally, 1-methoxy-2,7-octadiene under conditions sufficient to yield a catalyst precursor solution wherein the tertiary phosphine ligand is represented formulaically as $R^1PR^2$ and where $R^1$ is an aryl moiety or a substituted aryl moiety or an alkyl moiety or heteroatom-containing alkyl moiety wherein the heteroatom is oxygen with 1 to 12 carbon atoms, and $R^2$ is independently a heterocyclic oxaadamantyl group.

Phosphine-containing heterocyclic oxaadamantyl groups ($PR^2$) are suitably represented schematically as shown below wherein $R^1$ is as defined above:

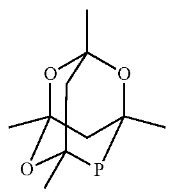

An illustrative heterocyclic oxaadamantyl ligand is 1,3,5,7-tetramethyl-6-phenyl-2,4,8-trioxa-6-phosphaadamantane (TMPTPA):

In some aspects, the conditions sufficient to yield a catalyst precursor solution include a temperature within a range of from 0 degrees centigrade (° C.) to 100° C., preferably from 5° C. to 60° C.

In some aspects, the number of equivalents of a phosphine is one or two.

In some aspects, the solvent blend has a 1-methoxy-2,7-octadiene content within a range of from 0.1 weight percent (wt %) to 50 wt %, based upon total solvent blend weight. In related aspects, the solvent blend has a 1-methoxy-2,7-octadiene content within a range of from 10 wt % to 25 wt %, based upon total solvent blend weight.

In some aspects, the catalyst precursor solution has a palladium concentration that ranges from 0.02 wt % to 2 wt %, preferably from 0.02 wt % to 1.5 wt % more preferably from 0.1 wt % to 1 wt % and still more preferably from 0.25 wt % to 0.6 wt %, as palladium metal, based on total catalyst precursor solution weight.

In some aspects, the conditions sufficient to yield the above-noted precursor include concentrations of MOD-1 from 1 equivalent per palladium to 500 equivalents per palladium, temperatures that range from 0° C. to 100° C., and reaction times that range from 1 hour to 1000 hours. As a general rule, with an increase in either or both of temperature and MOD-1 concentration, precursor formation becomes more rapid. One may adjust either or both to provide a convenient time for the conversion. In general for commercial operation, it is convenient that the precursor be formed in 2-100 hours, although this is not absolutely necessary. Reaction times of 100 hours or less can be achieved at temperatures from 30° C. to 60° C., with concentrations of MOD-1 from 10-50 wt % (about 75-400 molar equivalents based on palladium at 0.1 weight percent). The processes of various aspects of this invention have utility in that they yield a catalyst precursor that requires little, preferably no, induction time before it enters into the telomerization reaction.

Ligands suitable for use in the process and in making the catalyst precursor include tertiary arylphosphines, formulaically represented as $Ar_nPR_{(3-x)}$, where n=1-3, and Ar is independently selected from a group consisting of substituted or unsubstituted aromatic groups. Illustrative substituents for substituted aromatic groups include alkyl, aryl, alkaryl, aralkyl, alkoxy, halo, silyl, and amino groups. The tertiary arylphosphines may be fused with other substituted or substituted carbocyclic or heterocyclic aromatic or aliphatic rings. R is selected from the group of substituted or unsubstituted alkyl, and may contain additional heteroatoms, such as oxygen, nitrogen, silicon, and sulfur. In the case where n=1, R groups may be connected to form carbo- or hetero-cyclic rings or polycarbo- or polyhetero-cyclic rings. Furthermore, R and Ar groups may be connected to form rings.

Other suitable ligands include tertiary phosphines represented formulaically as $R^1PR^2$ wherein $R^1$ is an aryl moiety or a substituted aryl moiety or an alkyl moiety or a heteroatom-containing alkyl moiety and $R^2$ is independently a heterocyclic oxaadamantyl group. Illustrative substituents for substituted aromatic groups include alkyl, aryl, alkaryl, aralkyl, alkoxy, halo, silyl, and amino groups. When $R^1$ is an alkyl group, suitable groups include primary, secondary or tertiary $C_1$-$C_{12}$ (one to twelve carbon atom(s)) groups, each of which may contain a heteroatom such as oxygen, nitrogen, silicon, and sulfur. In preparing catalyst precursor solutions, such other suitable ligands benefit from using a solvent blend that contains MOD-1, but some of them react fast enough without MOD-1 that their performance is acceptable.

Prepare a catalyst precursor solution by bringing together, at a minimum, a source of Pd, preferably palladium acetyl acetonate, one or more equivalents of a tertiary phosphine ligand, an alkanols, preferably methanol, and methoxyoctadiene, preferably 1-methoxy-2,7-octadiene, under conditions sufficient to make an amount of a catalyst precursor that contains or comprises palladium, tertiary arylphosphine ligand, and a ligand derived from the methoxyoctadiene and may be represented formulaically by $[(Ar_nPR_{(3-n)})_x PdY]^{0\ or\ +}$, where n=1-3, and x=1 or 2, and Y is a ligand derived from methoxyoctadiene. In some aspects of this invention, the ligand Y may be octadienyl. The conditions include those noted hereinabove.

In making the catalyst precursor solution, suitable amounts of methoxyoctadiene range from about 0.1 wt % (about 1 molar equivalent at 0.1 weight % palladium) to 50 wt %, (about 400 molar equivalents at 0.1 weight percent palladium) in each case the weight percent is based on total catalyst precursor solution weight. The solvent blend has a 1-methoxy-2,7-octadiene content that is preferably within a range of from 10 weight percent to 50 weight percent, based upon total solvent blend weight. At a minimum, the amount is sufficient to convert at least some of the above minimum components used in forming the catalyst precursor solution to the catalyst precursor, with an amount sufficient to convert all of such components to the catalyst precursor being preferred. In the latter instance, use an amount of the methoxyoctadiene that is at least an equivalent molar stoichiometric amount to the amount of palladium. For example, if Pd constitutes 0.1 wt % of the catalyst solution, then methoxyoctadiene should be present in an amount of at least 0.1 wt %, each wt % being based on total catalyst solution weight. Larger amounts of methoxyoctadiene relative to the amount of Pd can be, and frequently are, used to, among other things, lead to MOD-1 modified catalyst precursor formation at a faster rate than one can attain with equivalent molar stoichiometric amounts.

GENERAL EXPERIMENTAL PROCEDURE

In a general procedure for conducting the telomerization reaction, place di-n-butyl ether (GC internal standard) ($Bu_2O$), methanol, methylcyclohexane (MeCy) solvent, a precatalyst stock solution prepared as detailed below (1 milliliter (mL)) and 0.5 mL of a 0.01932 molar solution of sodium methoxide (sometimes referred to as sodium methylate) (NaOMe) in methanol in a Fischer-Porter bottle. Unless otherwise specified, effect reactions with MeOH present at a 14 molar level, adjusting other components (also known as "reagents") in the bottle to account for changes in reaction chemistry. Seal the bottle with a valve equipped with a septum port. Outside a glove box, distill approximately 5 mL of butadiene into a gas-tight syringe, determining the actual amount of butadiene in the syringe by weighing the syringe before and after injecting the butadiene into the bottle through the septum with the syringe needle placed below the surface of bottle contents. Place the butadiene-containing bottle in a preheated oil bath (40° C., 60° C. or 70° C. as shown below) equipped with a magnetic stirrer bar and allow the contents of the bottle to react for a select period of time (e.g. 4 hours). Sample bottle contents at 30 minutes, 1 hour, 2 hours and 4 hours after initiating reaction to develop a conversion versus time profile to determine whether there is an induction period or not. Use a 24 inch (61 cm) needle equipped with a gas-tight valve to draw the samples from the bottle for use in gas chromatography analysis.

Example (Ex) 1: Preparation of TCMPP Pre-Catalyst Stock Solution

Using a glove box, dissolve 0.0147 gram (g) (0.0000483 mole) of palladium acetyl acetonate [(Pd(acac)$_2$], 0.0440 g (0.0000966 mole) of ligand, 0.134 g (0.00096 mole) of MOD-1, and 0.25 mL of a stock solution of acetic acid (AcOH) in methanol (0.1932 M) in approximately 24.75 mL methanol to a total volume of 25 mL and allow the resulting precatalyst stock solution to stir at ambient temperature (nominally 25° C.) for at least three days before use. Represent the ligand schematically as:

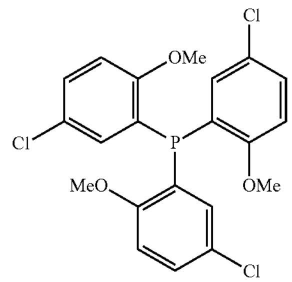 [SMILES: COc1ccc(Cl)cc1P(c1cc(Cl)ccc1OC)c1cc(Cl)ccc1OC]

Comparative Example (CEx) A

Make a pre-catalyst stock solution as in Ex 1, but omit the MOD-1.

Ex 2

Conduct a telomerization reaction at 40° C. using the pre-catalyst stock solution prepared in Ex 1. Show analytical results in Table 1 below.

TABLE 1

| Time | Butadiene Conversion (%) | MOD-1 Selectivity (%) | MOD-1 Yield (%) |
|---|---|---|---|
| 30 min | 43.2/44.1 | 97.3/97.2 | 42.0/42.9 |
| 1 hour | 47.8/49 | 97.3/97.2 | 46.5/47.7 |
| 2 hours | 53.2/54.5 | 97.3/97.5 | 51.7/53.1 |
| 4 hours | 61.4/69.3 | 97.2/97.3 | 59.7/67.4 |

CEx B

Replicate Ex 2 but with an aliquot of the pre-catalyst stock solution prepared in CEx A. Show analytical results in Table 2 below.

TABLE 2

| Time | Butadiene Conversion (%) | MOD-1 Selectivity (%) | MOD-1 Yield (%) |
|---|---|---|---|
| 30 min | 17.2 | 96.6 | 16.6 |
| 1 hour | 22.9 | 97.0 | 22.2 |
| 2 hours | 20.2 | 96.7 | 19.5 |
| 4 hours | 26.9 | 96.8 | 26.0 |

CEx C

Replicate Ex 1, but change the amount of MOD-1 from 10 equivalents to about 1200 equivalents per palladium and use one molar equivalent of TCMPP per molar equivalent of $Pd(acac)_2$.

CEx D

Replicate Ex 3, but Omit the MOD-1. lCEx E

Conduct a telomerization reaction at 70° C. with an aliquot of the pre-catalyst solution prepared in CEx C. Show analytical results in Table 3 below.

TABLE 3

| Time | Butadiene Conversion (%) | MOD-1 Selectivity (%) | MOD-1 Yield (%) |
|---|---|---|---|
| 30 min | 30.9 | 92.1 | 28.4 |
| 1 hour | 48.9 | 96.6 | 47.2 |
| 2 hours | 68.8 | 96.6 | 66.5 |
| 4 hours | 69.8 | 96.5 | 67.4 |

CEx F

Conduct a telomerization reaction at 70° C. with an aliquot of the pre-catalyst solution prepared in CEx D. Show analytical results in Table 4 below.

TABLE 4

| Time | Butadiene Conversion (%) | MOD-1 Selectivity (%) | MOD-1 Yield (%) |
|---|---|---|---|
| 30 min | 60.5/44.8 | 96.5/96.1 | 58.3/43.1 |
| 1 hour | 65.9/44.6 | 96.3/96 | 63.4/42.8 |
| 2 hours | 72.3/45.5 | 96.2/96 | 70.0/43.7 |
| 4 hours | 77.5/44.9 | 96.2/96 | 74.6/43.1 |

These comparative examples are included to demonstrate the conditions for which the MOD-1 modification of the precatalyst is ineffective. In these examples, the MOD-1-modified pre-catalyst is less efficient and converts less butadiene than the unmodified counter example. It is likely that there is a significant inhibition of MOD-1 within this regime of 1000+ equivalents of MOD-1 to palladium.

Ex 3

Replicate Ex 1, but use the ligand 1,3,5,7-tetramethyl-6-phenyl-2,4,8-trioxa-6-phosphaadamantane (TMPTPA) represented schematically below instead of TCMPP.

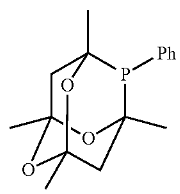

Prepare two pre-catalyst stock solutions from this solution:

Ex 3.1

For the first pre-catalyst stock solution, take 5 mL of the 25 mL solution and add (0.0170 g, 0.000122 moles) of MOD-1 to provide a pre-catalyst stock solution.

Ex 3.2

For the second pre-catalyst stock solution, use aliquots of the stock solution of Ex 3 as prepared.

Ex 4

Conduct a telomerization reaction at 40° C. using an aliquot of the pre-catalyst stock solution prepared in Ex 5.1. Show analytical results in Table 5 below.

TABLE 5

| Time | Butadiene Conversion (%) | MOD-1 Selectivity (%) | MOD-1 Yield (%) |
|---|---|---|---|
| 30 min | 13.4 | 93.6 | 12.5 |
| 1 hour | 33.1 | 95.5 | 31.6 |
| 2 hours | 45.1 | 95.3 | 42.9 |
| 4 hours | 56.9 | 95.1 | 54.1 |

CEx G

Replicate Ex 4, but use an aliquot of the pre-catalyst stock solution of Ex 3.2. Show analytical results in Table 6 below.

TABLE 6

| Time | Butadiene Conversion (%) | MOD-1 Selectivity (%) | MOD-1 Yield (%) |
|---|---|---|---|
| 30 min | 1.9 | 61.6 | 1.2 |
| 1 hour | 2.0 | 65.8 | 1.3 |
| 2 hours | 4.8 | 84.1 | 4.0 |
| 4 hours | 44.0 | 95.2 | 41.9 |

Ex 5

Use the pre-catalyst stock solution from Ex 3.1 but change the general procedure to include 1.0 mL of the sodium methoxide stock solution and 12 mL of methanol. Run the telomerization reaction at 40° C. Show analytical results in Table 7 below.

TABLE 7

| Time | Butadiene Conversion (%) | MOD-1 Selectivity (%) | MOD-1 Yield (%) |
|---|---|---|---|
| 30 min | 41.1 | 96.0 | 39.5 |
| 1 hour | 51.5 | 95.7 | 49.2 |
| 2 hours | 65.1 | 95.3 | 62.0 |
| 4 hours | 76.7 | 95.1 | 72.9 |

CEx H

Replicate Ex 5 but use the pre-catalyst stock solution from Ex 3.2. Show analytical results in Table 8 below.

TABLE 8

| Time | Butadiene Conversion (%) | MOD-1 Selectivity (%) | MOD-1 Yield (%) |
|---|---|---|---|
| 30 min | 3.1 | 76.3 | 2.4 |
| 1 hour | 7.3 | 88.2 | 6.4 |
| 2 hours | 9.6 | 90.3 | 8.7 |
| 4 hours | 65.3 | 95.1 | 62.1 |

Ex 6

Replicate Ex 1, but use the ligand TMPTPA at half the molar concentration of ligand.

CEx I

Replicate Ex 6 but without the addition of MOD-1.

Ex 7

Conduct a telomerization reaction at 40° C. using an aliquot from the pre-catalyst stock solution from Ex 6. Show analytical results in Table 9 below.

TABLE 9

| Time | Butadiene Conversion (%) | MOD-1 Selectivity (%) | MOD-1 Yield (%) |
|---|---|---|---|
| 30 min | 64.1 | 94.7 | 60.7 |
| 1 hour | 77.9 | 95.2 | 74.9 |
| 2 hours | 84.1 | 95.1 | 80.0 |
| 4 hours | 90.0 | 95.0 | 85.5 |

CEx J

Conduct a telomerization reaction at 40° C. with an aliquot of the pre-catalyst solution from CEx I. Show analytical results in Table 10 below.

TABLE 10

| Time | Butadiene Conversion (%) | MOD-1 Selectivity (%) | MOD-1 Yield (%) |
|---|---|---|---|
| 30 min | 33.6 | 92.9 | 31.2 |
| 1 hour | 54.3 | 94.6 | 51.4 |
| 2 hours | 71.0 | 95.0 | 67.4 |
| 4 hours | 81.3 | 94.7 | 77.0 |

Ex 8

Replicate Ex 1, but change the ligand to 1,3,5,7-tetramethyl-6-(2-methoxyphenyl)-2,4,8-trioxa-6-phosphaadamantane (TMPTPA-OMe), represented schematically below, change the amount of equivalents of MOD-1 to 10, and reduce the molar equivalents of TMPTPA-OMe to half (one equivalent per Pd):

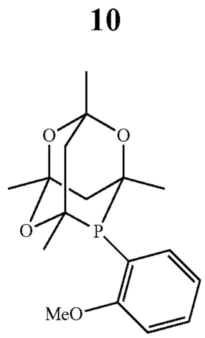

CEx K

Replicate Ex 8, but omit the MOD-1.

Ex 9

Conduct at telomerization reaction at 40° C. with an aliquot of the pre-catalyst solution prepared in Ex 8. Show analytical results in Table 11 below.

TABLE 11

| Time | Butadiene Conversion (%) | MOD-1 Selectivity (%) | MOD-1 Yield (%) |
|---|---|---|---|
| 30 min | 15.2 | 95.1 | 14.5 |
| 1 hour | 36.3 | 96.4 | 35.0 |
| 2 hours | 63.6 | 96.7 | 61.5 |
| 4 hours | 81.2 | 96.7 | 78.5 |

CEx L

Conduct a telomerization reaction at 40° C. with an aliquot of the pre-catalyst solution prepared in CEx K. Show analytical results in Table 12 below.

TABLE 12

| Time | Butadiene Conversion (%) | MOD-1 Selectivity (%) | MOD-1 Yield (%) |
|---|---|---|---|
| 30 min | 1.5 | 74.0 | 1.1 |
| 1 hour | 4.6 | 89.9 | 4.1 |
| 2 hours | 18.2 | 95.4 | 17.4 |
| 4 hours | 50.7 | 96.5 | 48.9 |

Ex 10

Conduct at telomerization reaction at 70° C. with an aliquot of the pre-catalyst solution prepared in Ex 8. Show analytical results in Table 13 below.

TABLE 13

| Time | Butadiene Conversion (%) | MOD-1 Selectivity (%) | MOD-1 Yield (%) |
|---|---|---|---|
| 30 min | 70.9 | 94.9 | 67.3 |
| 1 hour | 83.4 | 95.0 | 79.2 |
| 2 hours | 90.2 | 94.9 | 85.6 |
| 4 hours | 93.0 | 94.9 | 88.3 |

CEx M

Conduct a telomerization reaction at 70° C. with an aliquot of the pre-catalyst solution prepared in CEx K. Show analytical results in Table 14 below.

TABLE 14

| Time | Butadiene Conversion (%) | MOD-1 Selectivity (%) | MOD-1 Yield (%) |
|---|---|---|---|
| 30 min | 55.5 | 94.5 | 52.4 |
| 1 hour | 73.6 | 94.5 | 69.6 |
| 2 hours | 89.0 | 94.5 | 84.1 |
| 4 hours | 95.3 | 94.5 | 90.1 |

Several points of note emerge from a review of the above examples and comparative examples. First, addition of MOD-1 to methanol to create a solvent blend results in at least a substantial decrease in duration and in some cases elimination of an induction period before the catalyst precursor is ready to take an active part in telomerization. Second, use of a solvent blend (methanol and MOD-1) in preparation of telomerization catalyst precursor results in an increase in overall conversion of butadiene at a reaction temperature below 70° C. relative to conversion obtained with a telomerization catalyst precursor prepared in the absence of MOD-1 (methanol only) of at least 10%. Third, the telomerization catalyst precursor is stable in that it does not form solids that precipitate out of solution under the conditions stated in the examples (Ex 1-12) whereas under the same conditions save for use of methanol rather than a blend of methanol and MOD-1, a visually discernible amount of telomerization catalyst precursor effectively precipitates out of solution. The enhanced stability of the inventive telomerization catalyst precursor has an economic benefit in that one may decrease the amount of ligand used in its preparation.

Ex 11

Preparation of MOD-1 Modified Catalysts

Use a 1 gallon laboratory reactor to prepare the pre-catalyst solution. Operate the reactor with a reactor jacket set point temperature of 35° C., and a methanol condenser set point temperature of 5° C. Load the reactor with 53.9 g TCMPP and 17.9 g $Pd(acac)_2$, and then purge the reactor with $N_2$ at 0.5 scfh (14.2 liters/hour). Load the solvent reservoir with 1480.5 g methanol and sparge the reservoir with $N_2$. Transfer 419 g methanol to the reactor at 18 mL/min over 30 min. Start agitation of reactor contents at 580 rpm. Transfer an additional 838 g of methanol to the reactor at 152 mL/min over 7 min Add aqueous acetic acid solution (3.71 g acetic acid+1.59 g water) to the reactor with continued agitation. Add remaining methanol (223.5 g) to the reactor at 151 mL/min over 6 min, followed by 493.5 g of MOD-1. Reduce the reactor $N_2$ purge rate to 0.15-0.25 scfh (4.3-7.1 liters/hour). The overall pre-catalyst composition is designated as: Pd/TCMPP/acetic acid molar ratio of 1.00/2.01/1.04 and palladium concentration of 0.31 wt %. Allow the pre-catalyst solution to stir at 35° C. over 22 days at 580 rpm, sampling the pre-catalyst solution on days 1, 8, 15 and 22 for telomerization activity evaluation. Visual observation shows no evidence of solids precipitation over a period of 578 hours.

Take samples of the reactor contents on Day 1 using Pressure-Lok™ gas-tight syringes, and transfer the samples to a glove box maintained at less than 1 ppm oxygen. Periodically determine composition of such samples by $P^{31}$ NMR spectroscopy (400 megahertz (MHz) at −40° C. over an acquisition time of two to four hours, adding approximately 10% of $D_4$-methanol as a lock solvent). Control reactor content temperature either by a heated solvent bath, or by the glove box air-conditioner. Periodically take temperature measurements over the timescale of the reactions to confirm that temperature is controlled to ±1° C. In some cases, add an internal standard, triphenylphosphine oxide, so that absolute concentrations can be determined. See Table 15 below for $P^{31}$ NMR composition data.

TABLE 15

| Time (hrs) | Mole fraction of phosphorus by species*: TCMPP | TCMPP Oxide | Phosphonium | Initial Pre-catalyst | MOD-1 Modified Catalyst | Other Unidentified |
|---|---|---|---|---|---|---|
| 0 | 0.02 | 0.04 | 0.00 | 0.91 | 0.00 | 0.03 |
| 16 | 0.01 | 0.04 | 0.02 | 0.77 | 0.15 | 0.01 |
| 23 | 0.02 | 0.03 | 0.05 | 0.66 | 0.24 | 0.00 |
| 49 | 0.00 | 0.06 | 0.13 | 0.12 | 0.68 | 0.00 |
| 64 | 0.00 | 0.03 | 0.16 | 0.00 | 0.82 | 0.00 |
| 333 | 0.00 | 0.07 | 0.13 | 0.00 | 0.77 | 0.03 |

*TCMPP if free ligand, TCMPP Oxide is the phosphine oxide, Phosphonium is $[(2\text{-OMe}, 5\text{-Cl—}C_6H_3)_3P(CH_2CH{=}CHCH_2CH_2CH_2CH{=}CH_2)]^+$, Initial precatalyst is $\{(2\text{-OMe}, 5\text{-Cl—}C_6H_3)_3P\}_2Pd(\text{acetyl acetoante})]^+$, MOD-1 modified catalyst is $[(Ar_nPR_{(3-n)})_xPdY]$, This Ex 11 (with MOD-1 addition) shows that the initial pre-catalyst is converted to a MOD-1 modified catalyst over about 70 hours, after which no further significant changes occur. There is no discernible evidence showing formation of $[Pd(TCMPP)_2(CH_2{=}C\{(C{=}O)Me\}_2]$.

Table 16 below shows the catalyst activity and selectivity of the MOD-1 modified catalyst compared with the performance of the control catalyst that was not treated with MOD-1.

TABLE 16

| Reaction Time | Butadiene Conversion (%) Control: No MOD-1 Pre-treatment on Day 1 | Butadiene Conversion (%) after Catalyst Aging with MOD-1 for: 1 Day | 8 Days | 15 Days | 22 Days |
|---|---|---|---|---|---|
| 12-15 min | 3.3 | 20.1 | 58.2 | 65.5 | 66.3 |
| 45 min | 24.5 | 52.0 | 67.0 | 74.5 | 72.7 |
| 80-90 min | 50.8 | 67.7 | 73.7 | 77.2 | 80.2 |
| 130-150 min | 67.9 | 79.9 | 81.6 | 83.4 | 82.0 |
| 220-240 min | 76.9 | 84.3 | 85.6 | 86.7 | 84.8 |
| Final MOD-1 Selectivity (%) | 96.4 | 95.8 | 93.3 | 96.6 | 96.3 |

This data shows that the pre-catalyst is converted to a new, stable complex, $[(Ar_nPR_{(3-n)})_xPdY]$, which exhibits improved activity at 60° C. in telomerization, with a decrease in an induction period.

CEx K-O: Solids Precipitation from Unmodified Pre-Catalyst Solutions

Replicate Ex 11 with changes in palladium complex as shown in Table 17 below and elimination of MOD-1. A visual examination of catalyst solutions shows that solids ($[Pd(TCMPP)_2(CH_2{=}C\{(C{=}O)Me\}_2)$) begin to precipitate out of solution at 338 hours in the 1 gallon reactor at 20° C. with an initial palladium concentration of approximately 0.31 weight percent. At a smaller scale in the glove box under otherwise similar conditions, precipitation out of solution begins at approximately 310 hours (CEx L). Table 17 below shows precipitation times of catalyst that have not been modified by MOD-1 addition.

TABLE 17

| Experiment | Temperature (° C.) | Initial Palladium Concentration (Weight % as Pd) | Time of first evidence of precipitation (hrs) | Concentration of $[Pd(TCMPP)_2(CH_2{=}C\{(C{=}O)Me\}_2]$ at time of precipitation(Weight %) |
|---|---|---|---|---|
| CEx K | 31 | 0.305 | 76 | 0.79 |
| CEx L | 30 | 0.305 | 115 | 0.57 |
| CEx M | 20 | 0.305 | 310 | 0.68 |
| CEx N | 31 | 0.153 | 82 | 0.70 |
| CEx O | 31 | 0.102 | 120 | 0.64 |

CEx K-O show that, absent modification with MOD-1, solids precipitation occurs, such that the initially formed pre-catalyst is converted to a new, largely insoluble species, $[Pd(TCMPP)_2(CH_2{=}C\{(C{=}O)Me\}_2]$. The insoluble species can, in turn, foul process equipment.

CEx P

Add 2 wt % of isolated, solid $[Pd(TCMPP)_2(CH_2{=}C\{(C{=}O)Me\}_2]$ to a freshly prepared pre-catalyst solution and stir for half an hour in a glove box to allow dissolution of the solid and to achieve solid-liquid equilibrium Immediate $P^{31}$ NMR analysis shows a palladium (0) complex concentration in solution at room temperature (nominally 20° C.) of 0.08 wt %.

Ex 12

In a glovebox, dissolve degassed glacial acetic acid (AcOH) (55.3 µL) in degassed MeOH to a volume of 5 mL (0.1932 M AcOH in MeOH) to form AcOH solution. Dissolve palladium(II) acetylacetonate ($Pd(acac)_2$) (0.0110 g, 0.0000362 moles), 2,3-(dihydrobenzofuran-7-yl)diphenylphosphine (DHBDPP, illustrated below) (0.0220 g, 0.0000724 moles) and 0.1875 mL of the AcOH solution in 15.0 mL MeOH and 3.6 mL MOD-1 to form a precatalyst stock solution. Allow the precatalyst solution to stir for 6 days at 25° C. before use.

Add dibutyl ether ($Bu_2O$, 5 mL), 12.8 M MeOH (10.96 mL), anhydrous degassed methylcyclohexane (MeCy, 1.6 mL), the precatalyst stock solution (1 mL), and a portion of a solution of sodium methoxide (NaOMe) (1.0 mL) in MeOH (0.01932 M) to a Fisher-Porter bottle. Seal the Fisher-Porter bottle with a valve equipped with a septum port.

Use the above-noted General Experimental Procedure, a temperature of 40° C., a reaction time of 4 hours and sampling at 30 minutes, 60 minutes, 120 minutes and 240 minutes followed by GC analysis to evaluate performance of the MOD-1 modified pre-catalyst. See Table 18 below for a summary of such performance.

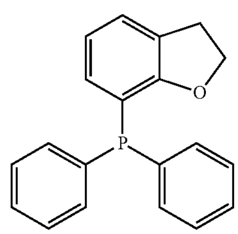

DHBDPP

CEx Q

Replicate Ex 12, but eliminate the MOD-1 addition, and change the amounts of palladium(II) acetylacetonate ($Pd(acac)_2$) to 0.0980 g (0.00003217 mole), DHBDPP to 0.0196 g (0.00006441 mole) and AcOH solution to 0.167 mL AcOH in 16.5 mL MeOH.

Ex 13

Replicate Ex 12, but change the oil bath temperature to 60° C.

CEx R

Replicate CEx Q, but change the oil bath temperature to 60° C.

Ex 14

Replicate Ex 12, but with the following changes: in making the precatalyst solution, use the following amounts: 0.0147 g (0.0000483 mole) of $Pd(acac)_2$, 0.250 mL of AcOH stock solution, 20 mL MeOH and 4.75 mL MOD-1; substitute triphenylphosphine (TPP, shown schematically below) (0.0253 g, 0.0000965 moles) for DHBDPP; allow the pre-catalyst to age for 7 days before use; and, in loading the Fisher-Porter bottle, use 0.5 mL of a solution of sodium methoxide in MeOH (0.01932 M) and 11.46 mL MeOH.

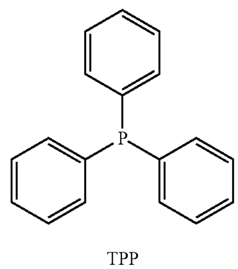

TPP

CEx S

Replicate Ex 1, but with the following changes: in making of the precatalyst solution, use the following amounts: 0.0147 g (0.0000483 miles) of $Pd(acac)_2$, 0.250 mL of AcOH stock solution and 24.75 mL MeOH. Substitute TPP (0.0253 g, 0.0000965 moles) for DHBDPP. In loading the Fisher-Porter bottle, use 0.5 mL of a solution of sodium methoxide in MeOH (0.01932 M) and 11.46 mL MeOH.

Ex 15

Replicate Ex 14, but heat the oil bath 60° C.

CEx T

Replicate CEx S, but heat the oil bath 60° C.

TABLE 18

| Ex | Ligand | MOD-1 | [MeOH] | NaOMe:Pd | L:Pd | Butadiene Conversion (%) 30 min | 1 hr | 2 hr | 4 hr | Final MOD-1 Selectivity (%) |
|---|---|---|---|---|---|---|---|---|---|---|
| Ex 12 | DHDDPP | Yes | 12.7 | 10:1 | 2:1 | 17.1 | 30.0 | 45.4 | 62.0 | 96.6 |
| C Ex Q | DHDDPP | N | 12.7 | 10:1 | 2:1 | 7.1 | 19.0 | 37.7 | 60.4 | 96.6 |
| Ex 13 | DHDDPP | Yes | 12.7 | 10:1 | 2:1 | 38.4 | 55.4 | 74.3 | 83.8 | 95.0 |
| C Ex R | DHDDPP | N | 12.7 | 10:1 | 2:1 | 17.4 | 36.7 | 65.3 | 83.4 | 95.2 |
| Ex 14 | TPP | Yes | 12.7 | 5:1 | 2:1 | 7.0 | 13.4 | 24.7 | 43.2 | 95.6 |
| C Ex S | TPP | N | 12.7 | 5:1 | 2:1 | 2.7 | 6.8 | 18.2 | 38.6 | 95.0 |
| Ex 15 | TPP | Y | 12.7 | 5:1 | 2:1 | 25.2 | 40.6 | 62.5 | 80.7 | 93.2 |
| C Ex T | TPP | N | 12.7 | 5:1 | 2:1 | 8.0 | 31.2 | 62.0 | 80.5 | 92.8 |

The data in Table 18 illustrate several points. First, the addition of MOD-1 to pre-catalyst solutions of DHDDPP and TPP generates catalytically competent complexes that result in a much faster initial rate of butadiene conversion than the pre-catalyst solutions that do not contain MOD-1 (compare the 30 min time points for all examples in Table 18). Second, the addition of MOD-1 to the pre-catalyst solutions of DHDDPP and TPP results in a higher overall conversion to products after the 4 hour reaction time. Third, the MOD-1 modification of the pre-catalyst does not affect the selectivity of the process. Thus, the modification of pre-catalyst solutions of DHDDPP and TPP with MOD-1 ultimately results in a higher yield of the desired product for all the demonstrated cases.

What is claimed is:

1. A process for telomerizing butadiene, the process comprising: preparing a telomerization catalyst precursor used in telomerization of butadiene that comprises dissolving one equivalent of palladium acetyl acetonate and from one to three equivalents of a phosphine in a solvent blend that comprises methanol and 1-methoxy-2,7-octadiene at a temperature within a range of from 0 degrees centigrade to 100 degrees centigrade to yield a catalyst precursor solution that comprises an aryl phosphine-palladium octadienyl complex represented formulaically either as $[(Ar_nPR_{(3-n)})_xPdY]$ or as $[(Ar_nPR_{(3-n)})_xPdY]^+$ wherein R is an alkyl or heteroatom-containing alkyl moiety with 1 to 12 carbon atoms, Ar is an aryl moiety or substituted aryl moiety, x=1 or 2, n=1, 2 or 3, and Y is a I-methoxy-2,7-octadiene ligand where no charge is present or octadienyl when a positive charge is present; and combining at least the telomerization catalyst precursor with butadiene to telomerize the butadiene.

2. The process of claim 1, wherein the conditions include a temperature within a range of from 5 degrees centigrade to 60 degrees centigrade.

3. The process of any of claims 1 through 2, wherein the number of equivalents of a phosphine is one or two.

4. The process of claim 1, wherein the solvent blend has a 1-methoxy-2,7-octadiene content within a range of from 0.1 weight percent to 50 weight percent, based upon total solvent blend weight.

5. The process of claim 4, wherein the solvent blend has a 1-methoxy-2,7-octadiene content within a range of from 10 weight percent to 25 weight percent, based upon total solvent blend weight.

6. The process of claim 1, wherein the catalyst precursor solution has a palladium concentration that ranges from 0.02 weight percent to 2 weight percent, as palladium metal, based on total catalyst precursor solution weight.

7. The process of claim 6 wherein the catalyst precursor solution has a palladium concentration that ranges from 0.1 weight percent to 1 weight percent, as palladium metal, based on total catalyst precursor solution weight.

8. The process of claim 1, wherein the telomerization catalyst precursor remains in solution for a period of at least 360 hours at a temperature within a range of from 5° C. to 60° C. and a palladium concentration exceeding 0.1 weight percent.

9. The process of claim 1, wherein the telomerization catalyst precursor does not include butadiene.

* * * * *